United States Patent [19]

Kees

[11] Patent Number: 4,764,623
[45] Date of Patent: Aug. 16, 1988

[54] N-(1H-TETRAZOL-5-YL-ALKYLPHENYL)-POLYFLUOROALKANAMIDES

[75] Inventor: Kenneth L. Kees, West Chester, Pa.

[73] Assignee: American Home Products Corporation, New York, N.Y.

[21] Appl. No.: 62,270

[22] Filed: Jun. 15, 1987

[51] Int. Cl.$^4$ ............................................. C07D 257/04
[52] U.S. Cl. .................................. 548/253; 514/884; 514/866
[58] Field of Search .............................. 548/252, 253

[56] References Cited

U.S. PATENT DOCUMENTS 3,894,033  7/1975  Holland ............................ 546/210
4,216,330  8/1980  Shepherd .......................... 548/254

OTHER PUBLICATIONS

Stout, Metabolism 34, 7 (1985).
Fujita et al., Diabetes 32, 804 (1983).
Sohda et al., Chem. Pharm. Bull. 32(6) 2267 (1984).

Primary Examiner—Glennon H. Hollrah
Assistant Examiner—D. B. Springer
Attorney, Agent, or Firm—Richard K. Jackson

[57] ABSTRACT

Compounds of the formula:

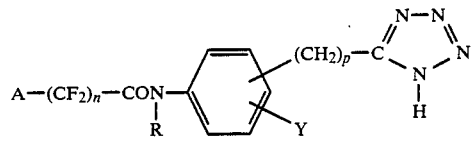

where R is hydrogen or A—$(CF_2)_m$—$CH_2$—; A is —F or —H; n is an integer from 1 to 10, inclusive; m is an integer from 0 to 9, inclusive; p is an integer from 0 to 4, inclusive; and Y is hydrogen, halo, trifluoromethyl, alkyl of 1 to 6 carbon atoms, alkoxy of 1 to 6 carbon atoms, or hydroxy; or a pharmaceutically acceptable salt thereof. The compounds are useful as anti-hyperglycemic and anti-hyperinsulinemic agents.

17 Claims, No Drawings

N-(1H-TETRAZOL-5-YL-ALKYLPHENYL)POLY-FLUOROALKANAMIDES

BACKGROUND OF THE INVENTION

Hyperinsulinemia, occurring in diabetics as well as non-diabetics, has been linked with coronary artery disease and disease of cerebral arteries as well as those of the lower limbs. Recent studies have linked elevated insulin levels with the development and support of lesions in both medium-sized and large arteries such as coronary arteries. Coronary heart diseases, including myocardial infarction and atherosclerosis, have been related to hyperinsulinemia. Hence, means for effective reduction of insulin levels and controlling glucose levels in diabetic as well as non-diabetic patients remains a desirable goal (Stout, Metabolism 34, 7 (1985)).

Ciglitazone [5-[4-(1-methylcyclohexylmethoxy)benzyl]-thiazolidine-2,4-dione] is currently considered one of the most unique and promising drugs for treatment of hyperglycemia and hyperinsulinemia (Fujita et al., Diabetes 32, 804 (1983)) because it only normalizes these parameters.

U.S. Pat. No. 4,216,330, granted Aug. 5, 1980, discloses a group of 4-(monoalkylamino)-benzonitriles and 5-[4-monoalkylamino)phenyl]tetrazoles as hypolipidemic agents useful in the treatment of atherosclerosis.

DESCRIPTION OF THE INVENTION

In accordance with this invention there is provided a group of compounds which possess excellent anti-hyperglycemic and anti-hyperinsulinemic activity of the formula:

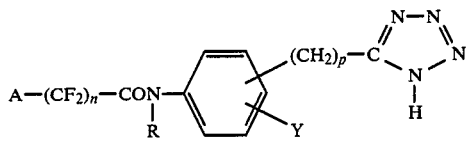

in which
R is hydrogen or $A-(CF_2)_m-CH_2-$;
A is $-F$ or $-H$;
n is an integer from 1 to 10, inclusive;
m is an integer from 0 to 9, inclusive;
P is an integer from 0 to 4, inclusive; and
Y is hydrogen, halo, trifluoromethyl, alkyl of 1 to 6 carbon atoms, alkoxy of 1 to 6 carbon atoms or hydroxy;
or a pharmaceutically acceptable salt thereof.

The pharmaceutically acceptable salts include the alkali metal or amine salts of 1H (or 2H) tetrazoles of this invention, such as the sodium, potassium, lower alkylamine, di (lower alkyl) amine, tri (lower alkyl) amine and the iv corresponding omega-hydrozy analogues (e.g. methylamine, ethylamine, propylamine, dimethylamine, diethylamine, dipropylamine, trimethylamine, triethylamine, tripropylamine, di (hydroxyethyl) amine, and the like. By "halo", Applicant intends to embrace $-Cl$, $-Br$, $-F$ and $-I$.

It is to be understood that the tetrazolyl moiety, depicted throughout this application as 1H-tetrazol-5-yl, is capable of tautomerization to the 2H-tetrazol-5-yl moiety, thusly:

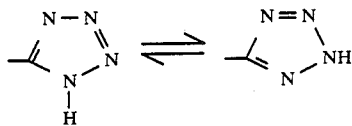

Hence, throughout this specification and claims, reference to the 1H tautomer is intended to also embrace the 2H tautomer.

The compounds of this invention can be prepared by conventional methods well within the skill of the medicinal chemist. For example, acylation of 4-aminobenzylcyanide with the desired perfluoroalkanoyl halide followed by reaction of the resulting nitrile with an alkali metal azide affords the claimed compounds. N-perfluoroalkylation can be achieved by known techniques such as by reductive alkylation using a perfluoro aldehyde or acylation with perfluoroalkanoyl halide followed by reduction with lithium aluminum hydride.

The following examples illustrate the production of representative compounds of the invention.

EXAMPLE 1

2,2,3,3,4,4,4-Heptafluoro-N-[4-(1H-tetrazol-5-ylmethyl)phenyl]butanamide

A mixture of 4-aminobenzylcyanide (9.2 g.), diisopropyl ethyl amine (10.8 g.) and dichloromethane (350 ml.) was cooled in an ice bath under a nitrogen atmosphere. To this mixture was added dropwise (neat) perfluorobutyryl chloride. The reaction mixture was allowed to warm gradually to room temperature and was stirred overnight at ambient temperature (15 hours). The mixture was then cooled in ice and stirred with 10% HCl solution. The solid was filtered off and washed with water. After air drying, the product was further dried in a vacuum for several hours. The 2,2,3,3,4,4,4-heptafluoro-N-[(4-cyanomethyl)phenyl]butanamide so obtained (17.5 g., 76%) was sufficiently pure for further use (homogeneous by thin layer chromatography, 70-30 hexaneethyl acetate). A sample recrystallized from dichloromethane yielded silvery plates, mp 116°-118° C.

A mixture of 2,2,3,3,4,4,4-heptafluoro-N-[4-(cyanomethyl)phenyl]butanamide (17.5 g.), sodium azide (17.3 g.) and ammonium chloride (14.1 g.) was heated in dimethylformamide (250 ml.) at 130°-135° C. (oil bath) under a nitrogen atmosphere for 20 hours. Enough water was then added to the hot reaction mixture to dissolve all suspended salts and the mixture was allowed to cool to room temperature. Additional water was then added to produce a white precipitate which was filtered, washed with water and dried under vacuum. The white solid 2,2,3,3,4,4,4-heptafluoro-N-[4-(1H-tetrazol-5-ylmethyl)phenyl]butanamide product (8.7 g., 44%, mp 176°-179° C.) was analytically pure as isolated. A sample recrystallized from acetone (minimum amount)/diethyl ether melted at 176°-178° C.

Elemental Analysis for: $C_{12}H_8F_7N_5O$: Calculated: C, 38.83; H, 2.17; N, 18.86; Found: C, 38.78; H, 2.41; N, 18.76.

EXAMPLE 2

2,2,3,3,4,4,5,5,6,6,7,7,8,8,8-Pentadecafluoro-N-[4-(1H-tetrazol-5-ylmethyl)phenyl]octanamide Following the procedure of Example 1, with the exception that perfluorooctanoyl chloride was employed as the acid halide reactant rather than perfluorobutyryl chloride, yielded the title compound, m.p. 193°–194° C.

Elemental Analysis for: $C_{16}H_8F_{15}N_5O \cdot \frac{1}{4}H_2O$: Calculated: C, 33,38; H, 1.49; N, 12.16; Found: C, 33.03; H, 1.38; N, 11.93.

EXAMPLE 3

2,2,3,3,4,4,5,5,6,6,7,7,8,8,9,9-Hexadecafluoro-N-[4-(1H-tetrazol-5-ylmethyl)phenyl]nonanamide Following the procedure of Example 1, with the exception that 2,2,3,3,4,4,5,5,6,6,7,7,8,8,9,9-hexadecafluorononanoyl chloride was employed as the acid halide reactant, yielded the title compound. Recrystallization from acetone diethyl ether gave, m.p. 187.5°–190.5° C.

Elemental Analysis for: $C_{17}H_9F_{16}N_5O$: Calculated: C, 33.85; H, 1.5; N, 11.61; Found: C, 33.69; H, 1.59; N, 11.58.

EXAMPLE 4

2,2,3,3,4,4,4-Heptafluoro-N-[2-(1H-tetrazol-5-ylmethyl)phenyl]butanamide

A mixture of 2-aminobenzylcyanide (15 g) [Rousseau et al., JACS 72, 3047 (1950)], diisopropylethylamine (16 g) and dichloromethane (400 mL) was cooled in an ice bath under a nitrogen atmosphere. Heptafluorobutyryl chloride (28.9 g) in dichloromethane (100 mL) was added dropwise and the reaction was left to warm gradually to room temperature overnight. A 10% aqueous HCl solution was added and the organic phase was separated and dried over MgSO4. After filtration and concentration with a rotary evaporator, the crude, orange oil (42 g) was purified by high pressure liquid chromatography to give 35.4 g of 2,2,3,3,4,4,4-heptafluoro-N-[2-(cyanomethyl)phenyl]butanamide as a white solid, m.p. 76°–79° C.

A mixture of 2,2,3,3,4,4,4-heptafluoro-N-[2-(cyanomethyl)phenyl]butanamide (15 g), sodium azide (14.85 g), ammonium chloride (12.22 g) and dimethylformamide (200 mL) was heated in a 130° C. oil bath under a nitrogen atmosphere overnight. The reaction mixture was cooled to room temperature, water (100 mL) was added and the product was extracted with ethylacetate (3×200 mL). The combined extracts were dried over Na2SO4, filtered and concentrated with a rotary evaporator. The brown residue was purified by high pressure liquid chromatography to give a white solid. The solid was triturated with diethyl ether to give 3.2 g of the title compound, m.p. 117°–178° C.

Elemental Analysis for: $C_{12}H_8F_7N_5O$: Calculated: C, 38.83; H, 2.17; N, 18.87; Found: C, 38.81; H, 2.14; N, 18.52.

EXAMPLE 5

2,2,3,3,4,4,4-Heptafluoro-N-[3-(1H-tetrazol-5-ylmethyl)phenyl]butanamide

Following the procedure of Example 4, with the exception that 3-aminobenzylcyanide was employed as the initial reactant, the title compound was obtained, m.p. 148°–151° C.

Elemental Analysis for: $C_{12}H_8F_7N_5O$: Calculated: C, 38.83; H, 2.17; N, 18.87; Found: C, 38.68; H, 2.25; N, 18.59.

EXAMPLE 6

2,2,3,3,4,4,5,5,6,6,7,7,8,8,8-Pentadecafluoro-N-[3-(1H-tetrazol-5-ylmethyl)phenyl]octanamide Following the procedure of Example 4, with the exceptions that 3-aminobenzylcyanide was employed as the initial reactant and perfluorooctanoyl chloride was employed as the acid halide, gave the title compound which was recrystallized from ethyl acetate/hexane, m.p. 163°–166° C.

Elemental Analysis for: $C_{16}H_8F_{15}N_5O$: Calculated: C, 33.64; H, 1.41; H, 12.26; Found: C, 33.83; H, 1.63; N, 11.88.

EXAMPLE 7

2,2,3,3,4,4,4-Heptafluoro-N-[4-(1H-tetrazol-5-yl)phenyl]butanamide

A mixture of 4-aminobenzonitrile (1.58 g), triethylamine (1.36 g), and dichloromethane (20 mL) was cooled in ice under a nitrogen atmosphere. To this mixture was added perfluorobutyryl chloride (3.11 g) in dichloromethane (10 mL) and the resulting mixture was allowed to warm to room temperature and was then stirred for three hours. The reaction mixture was diluted with HCl solution (1N, 50 mL) and the layers were partitioned in a separatory funnel. The organic phase was washed with a saturated brine solution, dried over MgSO4, filtered and concentrated with a rotary evaporator. The residue was dissolved in dichloromethane. Upon dilution with hexane the product precipitated to give 1.55 g of 2,2,3,3,4,4,4-heptafluoro-N-[4-(cyano)phenyl]butanamide, m.p. 116°–118° C.

A mixture of 2,2,3,3,4,4,4-heptafluoro-N-[4-(cyano)phenyl]butanamide (1.5 g,) sodium azide (1.55 g), ammonium chloride (1.28 g) and dimethylformamide (20 mL) was heated in a 130°–135° C. oil bath overnight. The reaction mixture was then poured onto 200 mL of water and the resulting solid was filtered off and recrystallized from ethanol. The product was dried at 100° C. overnight using an abderhalden (drying pistol) to give the title compound, m.p. 266°–268° C.

Elemental Analysis for: $C_{11}H_6F_7N_5O$: Calculated: C, 36.99; H, 1.69; N, 19.61; Found: C, 37.19; H, 1.90; N, 19.14.

EXAMPLE 8

2,2,2-Trifluoro-N-[4-(1H-tetrazol-5-ylmethyl)phenyl]acetamide

A mixture of 4-aminobenzylcyanide (20 g), diisopropylethylamine (19.6 g) and dichloromethane (400 mL) was cooled in ice under a nitrogen atmosphere. Trifluoro acetic anhydride (31.8 g) in dichloromethane (50 mL) was added dropwise and the reaction was allowed to warm gradually to ambient temperature overnight. The reaction mixture was diluted with ethyl acetate and washed successively with 5% HCl and saturated brine solutions, dried over MgSO4, filtered and concentrated with a rotary evaporator to give a tan solid (38.68 g), which was recrystallized from ethylacetate/hexane mixture to give 27 g (combined two crops) of 2,2,2-trifluoro-N-[(4-cyanomethyl)-phenyl]acetamide as tan crystals, m.p. 148°–150° C.

A mixture of 2,2,2-trifluoro-N-[(4-cyanomethyl)-phenyl]acetamide (7.49 g), sodium azide (10.67 g), ammonium chloride (8.78 g) and dimethylformamide (200 mL) were heated in a 130° C. oil bath under a nitrogen atmosphere overnight. Water was added until all suspended salts were dissolved and the mixture was partitioned between saturated aqueous brine solution and ethylacetate. The extracts were dried over MgSO$_4$, filtered and concentrated with a rotary evaporator to give 12.2 g of a tan oil. The product was purified by high pressure liquid chromatography, yielding 2,2,2-trifluoro-N-[(4-cyanomethyl)phenyl]acetamide as a white solid, m.p. 203°–206° C.

Elemental Analysis for: $C_{10}H_8F_3N_5O$: Calculated: C, 44.29; H, 2.97; N, 25.82; Found: C, 44.56; H, 3.16; N, 25.68.

EXAMPLE 9

2,2,3,3,3-Pentafluoro-N-[4-(1H-tetrazol-5-ylmethyl)-phenyl]propanamide

Following the procedure of Example 8, with the exception that perfluoropropionic acid anhydride was used as the acylating agent, the title compound was obtained, m.p. 183°–185° C.

Elemental Analysis for: $C_{11}H_8F_5N_5O$: Calculated: C, 41.13; H, 2.51; N, 21.80; Found: C, 41.19; H, 2.39; N, 21.45.

EXAMPLE 10

2,2,3,3,4,4,5,5,6,6,7,7,8,8,9,9,9-Heptadecafluoro-N-[4-(1H-tetrazol-5-ylmethyl)phenyl]nonanamide Perfluorononanoic acid (10 g), ethoxyacetylene (6 g) and ethylacetate were refluxed under a nitrogen atmosphere overnight. The reaction mixture was cooled to room temperature, 4-aminobenzylcyanide (3.43 g) was added in one portion and the resulting mixture was allowed to stir at room temperature for 24 hours. The precipitate was filtered, washed with hexane and dried under vacuum. The white solid (4.7 g) 2,2,3,3,4,4,5,5,6,6,7,7,8,8,9,9,9-heptadecafluoro-N-[(4-cyanomethyl)phenyl]nonanamide product melts at 172°–176° C.

A mixture of 2,2,3,3,4,4,5,5,6,6,7,7,8,8,9,9,9-heptadecafluoro-N-[(4-cyanomethyl)phenyl]nonanamide (4.6 g), sodium azide (2.59 g), ammonium chloride (2.1 g) and dimethylformamide (50 mL) were heated in a 135° C. oil bath under a nitrogen atmosphere overnight. Enough water was added to the hot reaction mixture so that all suspended salts dissolved and the resulting solution was cooled to room temperature. The white precipitate was collected by filtration and washed with water and hexane, sequentially. Air drying yielded 2.77 g (56%) of the title compound, m.p. 195°–198° C. (dec.).

Elemental Analysis for: $C_{17}H_8F_{17}N_5O$: Calculated: C, 32.87; H, 1.29; N, 11.27; Found: C, 32.82; H, 1.65; N, 11.

EXAMPLE 11

2,2,3,3,4,4,5,5,6,6,7,7,8,8,9,9,10,10,10-Nonadecafluoro-N-[4-(1H-tetrazol-5-ylmethyl)phenyl]decanamide Following the procedure of Example 10, with the exception that perfluorodecanoic acid was employed as the acylating agent, gave the title compound. Recrystallization from acetone gave m.p. 205°–209° C. (dec.).

Elemental Analysis for: $C_{18}H_8F_{19}N_5O$: Calculated: C, 32.21; H, 1.2; N, 10.43; Found: C, 32.14; H, 1.23; N, 10.29.

EXAMPLE 12

2,2,3,3,4,4,5,5,6,6,7,7,8,8,9,9,10,10,11,11-Eicosafluoro-N-[4-(1H-tetrazol-5-ylmethyl)phenyl]undecanamide Following the procedure of Example 10, with the exception that 2,2,3,3,4,4,5,5,6,6,7,7,8,8,9,9,10,10,11,11-perfluoroeicosanoic acid was employed as the acylating agent, gave the title compound. Recrystallization from acetone gave m.p. 199.5°–202° C. (dec.).

Elemental Analysis for: $C_{19}H_9F_{20}N_5O$: Calculated: C, 32.45; H, 1.29; N, 9.96; Found: C, 32.61; H, 1.42; N, 9.73.

EXAMPLE 13

2,2,3,3,4,4,5,5-Nonafluoro-N-[4-(1H-tetrazol-5-ylmethyl)phenyl]pentanamide

Perfluorovaleric acid (10 g), ethoxyacetylene (12.3 g) and ethyl acetate (175 mL) were stirred overnight at room temperature under a nitrogen atmosphere. 4-Aminobenzylcyanide (5.57 g) was added and the resulting mixture was allowed to stir at room temperature for 24 hours. The reaction mixture was cooled in ice and 10% aqueous HCl solution was added until a precipitate formed. The solid was collected and washed with water and hexane, sequentially, and dried in vacuo to yield 7.4 g (53%) of 2,2,3,3,4,4,5,5-nonafluoro-N-[4-(cyanomethyl)phenyl]pentanamide as a tan solid, m.p. 126°–128° C.

A mixture of 2,2,3,3,4,4,5,5-nonafluoro-N-[4-(cyanomethyl)phenyl]pentanamide (6.8 g), sodium azide (5.56 g), ammonium chloride (4.53 g) and dimethylformamide (100 mL) were heated in a 135° C. oil bath under a nitrogen atmosphere overnight. Enough water was added to the hot reaction mixture to dissolve all suspended salts, the mixture was cooled to room temperature and more water was added until a precipitate formed. The solid was collected, washed with water and air dried. Recrystallization from ethylacetate/diethyl ether mixture yielded 3.4 g of the title compound as white flakes, m.p. 173°–174° C. The filtrate produced a second crop of 1.1 g of the title compound.

Elemental Analysis for: $C_{13}H_8F_9N_5O$: Calculated: C, 37.07; H, 1.91; N, 16.63; Found: C, 36.92; H, 2.1; N, 16.66.

EXAMPLE 14

2,2,3,3,4,4,4-Heptafluoro-N-[4-(1H-tetrazol-5-ylethyl)-phenyl]butanamide

To a 0° C. solution of 2-[(4-amino)phenyl]ethanol (25 g), diisopropylethylamine (23.9 g) and dichloromethane (400 mL) was added heptafluorobutyryl chloride (41.8 g) dropwise over 0.5 hour. The mixture was allowed to warm gradually to room temperature and stirred for 2 hours. The precipitate was filtered off and the filtrate was diluted with ethylacetate (100 mL), washed with water (3×500 mL), dried over sodium sulfate, filtered and concentrated with a rotary evaporator. The residue was triturated with dichloromethane and collected by filtration. The combined solids were dissolved in diethyl ether and washed with water and saturated aqueous sodium chloride solutions, dried over sodium sulfate, filtered and concentrated to give 2,2,3,3,4,4,4-heptafluoro-N-[4-(2-hydroxyethyl)phenyl]butanamide as a white solid (39.2 g).

A mixture of 2,2,3,3,4,4,4-heptafluoro-N-[4-(2-hydroxyethyl)phenyl]butanamide (25 g), carbon tetrabromide (51 g), diethyl ether (140 mL) and tetrahydrofuran (140 mL) was cooled in ice and treated with triphenylphosphine (39.3 g), portionwise. When addition of the phosphine was complete, the reaction mixture was allowed to warm to room temperature and stirred for 2 hours. The precipitate was removed by filtration and the filtrate concentrated in vacuo. The residue was purified by chromatography on silica gel, eluted with dichloromethane to give 16.2 g of 2,2,3,3,4,4,4-heptafluoro-N-[4-(2-bromoethyl)phenyl]butanamide as a white solid.

A solution of 2,2,3,3,4,4,4-heptafluoro-N-[4-(2-bromoethyl)phenyl]butanamide (9.9 g), and sodium cyanide (1.72 g) in dimethylsulfoxide (50 mL) was stirred at room temperature under a nitrogen atmosphere for 24 hours. The mixture was treated with additional sodium cyanide (0.8 g) and the reaction was stirred for another 18 hours. The reaction mixture was poured into water (1 L) and extracted with diethyl ether. The extracts were washed with water and with saturated brine solution, dried over sodium sulfate, filtered and concentrated with a rotary evaporator. The crude orange residue was chromatographed on silica gel, eluted with a hexane-ethylacetate (7:3) mixture to give 4.2 g of 2,2,3,3,4,4,4-heptafluoro-N-[4-(2-cyanoethyl)phenyl]butanamide as a yellow solid.

A mixture of 2,2,3,3,4,4,4-heptafluoro-N-[4-(2-cyanoethyl)phenyl]butanamide (3.9 g), sodium azide (3.7 g), ammonium chloride (3 g) and dimethylformamide (60 mL) was stirred under a nitrogen atmosphere and heated in a 130° C. oil bath for 48 hours. Water (300 mL) was added to the hot mixture to dissolve all suspended salts and the solution was allowed to cool to room temperature. More water was added and the precipitate was collected by filtration. The tan solid was dried at 65° C. in vacuo overnight and recrystallized from a hexane/tetrahydrofuran mixture to give 1.9 g (43% yield) of the title compound as a tan solid, m.p. 161°–162° C.

Elemental Analysis for: $C_{13}H_{10}F_7N_5O$: Calculated: C, 40.53; H, 2.62; N, 18.18; Found: C, 40.59; H, 2.57; H, 17.93.

EXAMPLE 15

2,2,3,3,4,4,5,5,6,6,7,7,8,8,8-Pentadecafluoro-N-[4-(1H-tetrazol-5-ylpropyl)phenyl]octanamide To a mixture of 4-(4-nitro)phenylbutyric acid (1.05 g) in refluxing dichloromethane under a nitrogen atmosphere (10 mL) was added chlorosulfonyl isocyanate (722 mg) and the solution was refluxed for 2 hours. Cooling the reaction mixture to room temperature produced a solid. Dimethylformamide (852 μL) was added and the solution was stirred at room temperature for 1 hour. Water (50 mL) was added and the mixture was stirred vigorously for 1 hour and then extracted with dichloromethane. The organic phase was then washed successively with water, saturated aqueous sodium bicarbonate solution, water and saturated brine solution. Concentration gave 620 mg of 4-[(4-nitro)phenyl]butyrylnitrile as an oil.

To a mixture of 4-[(4-nitro)phenyl]butyrylnitrile (9.5 g) and ethylacetate (100 mL) was added stannous chloride dihydrate (56.4 g), in portions. The mixture was then warmed to reflux for 1.5 hour. The solution was cooled in ice and 25% aqueous sodium hydroxide was added until pH 14 was reached. The precipitated solids were removed by filtration and the filtrate was diluted with saturated brine solution and extracted with ethylacetate. The extracts were dried over sodium sulfate, filtered and concentrated with a rotary evaporator to give 4-[(4-amino)phenyl]butyrylnitrile (6.9 g) as a yellow oil.

A mixture of 4-[(4-amino)phenyl]butyrylnitrile (4 g), diisopropylethylamine (3.4 g) and dichloromethane (60 mL) was cooled in ice under a nitrogen atmosphere. Perfluorooctanoyl chloride (10.4 g) in dichloromethane (20 mL) was added and the solution was allowed to warm to ambient temperature. After 3 hours the precipitate was collected by filtration and washed with dichloromethane. The combined filtrates were diluted with ethylacetate, washed with 1N HCl and water and concentrated with a rotary evaporator. The residue was triturated with dichloromethane and collected by filtration. The combined solids were dried at 35° C. in vacuo overnight to give 10.1 g of 2,2,3,3,4,4,5,5,6,6,7,7,8,8,8-pentadecafluoro-N-[4-(3-cyanopropyl)phenyl]octanamide as a white solid.

A mixture of 2,2,3,3,4,4,5,5,6,6,7,7,8,8,8-pentadecafluoro-N-[4-(3-cyanopropyl)]octanamide (8.3 g), sodium azide (4.9 g), ammonium chloride (4 g) and dimethylformamide (90 mL) was heated in a 130° C. oil bath for 48 hours. Enough water was added to the hot mixture to dissolve all suspended salts and the solution was allowed to cool to room temperature. The precipitate was collected by filtration, washed successively with water and hexane and dried at 65° C. in vacuo for 2 hours. The product was recrystallized from a tetrahydrofuran/hexane mixture to give 5.8 g of the title compound as a white solid, m.p. 170.5°–172.5° C.

Elemental Analysis for: $C_{18}H_{12}F_{15}N_5O$: Calculated: C, 36.10; H, 2.03; N, 11.67; Found: C, 36.07; H, 2.02; N, 11.67.

EXAMPLE 16

2,2,3,3,4,4,4-Heptafluoro-N-[4-(1H-tetrazol-5-ylpropyl)phenyl]butanamide

Following the procedure of Example 15, with the exception that perfluorobutyryl chloride was employed as the acylating agent rather than perfluorooctanoyl chloride, gave the title compound. Recrystallization from tetrahydrofuran/hexane gave m.p. 143.5°–145° C.

Elemental Analysis for: $C_{14}H_{12}F_7N_5O$: Calculated: C, 42.11; H, 3.03; N, 17.54; Found: C, 42.48; H, 3.01; N, 17.48.

Sodium salts of the tetrazoles prepared in the preceding examples were prepared routinely by reaction with sodium hydroxide employing ethanol as a solvent. The reaction mixture was stirred at room temperature overnight under a nitrogen atmosphere. Volatile materials were removed in vacuo with a rotary evaporator and the residue was triturated with ethylacetate (except those cases in which the perfluoroacyl chain was four carbons or less). The solid material was collected by filtration, washed with ethylacetate (in which case diethyl ether was employed) and air dried. The following elemental analyses and melting points (where obtained) are for the sodium salts of the indicated products of the foregoing examples:

Example 1:
Na salt, m.p. 233° C. (dec.)

Elemental Analysis for: $C_{12}H_7F_7N_5ONa \cdot H_2O$: Calculated: C, 35.05; H, 2.21; N, 17.03; Found: C, 35.03; H, 2.31; N, 16.95.

Example 2:

Na salt, m.p. >270° C.

Elemental Analysis for: $C_{16}H_7F_{15}N_5ONa \cdot H_2O$: Calculated: C, 31.43; H, 1.15; N, 11.46; Found: C, 31.24; H, 1.25; N, 11.35.

Example 4:

Na salt, m.p. 146°–149° C.

Elemental Analysis for: $C_{12}H_7F_7N_5ONa \cdot \frac{1}{2}H_2O$: Calculated: C, 35.83; H, 2.0; N, 17.41; Found: C, 36.09; H, 1.99; N, 17.25.

Example 5:

Na salt, m.p. 155°–158° C.

Elemental Analysis for: $C_{12}H_7F_7N_5ONa \cdot \frac{1}{2}H_2O$: Calculated: C, 35.83; H, 2.0; N, 17.41; Found: C, 35.67; H, 2.11; N, 17.31.

Example 12:

Na salt, m.p. >220° C.

Elemental Analysis for: $C_{18}H_{11}F_{15}N_5ONa \cdot \frac{1}{2}H_2O$: Calculated: C, 34.30; H, 1.91; N, 11.11; Found: C, 34.34; H, 1.88; N, 11.04.

Other salts embraced by this disclosure are produced in similar ways well within the skill of the chemist.

The anti-hyperglycemic and anti-hyperinsulinemic activity of the compounds of this invention was established by subjecting them to the following standard experimental procedure for that purpose:

Eight to ten week old genetically obese (ob/ob) mice are randomly placed in groups of nine animals. The compound being tested is administered in single doses orally for four consecutive days. A blood sample is taken on the fifth day at the normal dosing time. The concentration of insulin and glucose in plasma obtained from the blood samples is determined and reported as the mean ± standard error for each test group of nine animals and compared to vehicle control and ciglitazone as the standard.

The results of these tests are as follows:

| Dose mg/kg | Glucose (mg/dl) | | | Insulin (μU/ml) | | |
|---|---|---|---|---|---|---|
| | Vehicle Control | Standard | Example | Vehicle Control | Standard | Example |
| 75 | 145 ± 10 | 100 ± 4* | 113 ± 6* (1, H) | 238 ± 14 | 79 ± 3* | 134 ± 13* (1, H) |
| 5 | 154 ± 10 | 106 ± 4* | 118 ± 6* (1, H) | 182 ± 9 | 128 ± 12* | 129 ± 17 (1, H) |
| 75 | | 89 ± 7* | 95 ± 6* (1, H) | | 57 ± 7* | 87 ± 10* (1, H) |
| 2 | 139 ± 8 | 133 ± 8 | 148 ± 15 | 167 ± 14 | 171 ± 9 | 165 ± 17 |
| 5 | | 127 ± 5 | 116 ± 7* | | 156 ± 12 | 185 ± 14 |
| 20 | | 114 ± 7* | 113 ± 7* | | 86 ± 5* | 139 ± 19 |
| 75 | | 89 ± 5* | 94 ± 7* (1, H) | | 67 ± 6* | 90 ± 18* (1, H) |
| 300 | 178 ± 18 | 92 ± 8* | 90 ± 4* (1, Na) | 206 ± 16 | 116 ± 18* | 61 ± 5* (1, Na) |
| 75 | 185 ± 29 | 75 ± 5* | 88 ± 5* (7) | 217 ± 22 | 113 ± 14* | 113 ± 14* (2) |
| | | | 100 ± 6* (2) | | | 191 ± 30 (3) |
| | | | 75 ± 4* (8) | | | 34 ± 4* (4) |
| | | | 96 ± 9* (2) | | | 139 ± 21* |
| 2 | 138 ± 11 | 132 ± 16 | 102 ± 9* | | | |
| 5 | | 106 ± 9* | 87 ± 6* (4) | | | |
| 75 | 138 ± 11 | 63 ± 3* | 92 ± 8* | 235 ± 26 | 61 ± 6* | 85 ± 17* |

*significantly different from control by unpaired test, p < 0.05.

| Dose mg/kg | Glucose (mg/dl) | | | Insulin (μU/ml) | | |
|---|---|---|---|---|---|---|
| | Vehicle Control | Standard | Example | Vehicle Control | Standard | Example |
| 20 | 115 ± 11 | 75 ± 5* | 75 ± 4* (2) | 179 ± 29 | 134 ± 16 | 101 ± 19* |
| 75 | | 66 ± 3* | 69 ± 4* (5) | | 65 ± 8* | 75 ± 12* (5) |
| 20 | 112 ± 7 | 89 ± 4* | 115 ± 8 | 217 ± 18 | 119 ± 17* | 182 ± 19 |
| | | | 86 ± 5* (3) | | | 66 ± 11* (3) |
| 5 | 137 ± 12 | 129 ± 7 | 100 ± 5* (2) | 211 ± 16 | 187 ± 17 | 149 ± 18* (2) |
| | | | 90 ± 7* (2, Na) | | | 167 ± 22 (2, Na) |
| 20 | | 98 ± 6* | 99 ± 3* (2) | | 134 ± 14* | 106 ± 7* (2) |
| | | | 79 ± 4** (2, Na) | | | 71 ± 6** (2, Na) |

-continued

| Dose mg/kg | Glucose (mg/dl) | | | Insulin (μU/ml) | | |
|---|---|---|---|---|---|---|
| | Vehicle Control | Standard | Example | Vehicle Control | Standard | Example |
| 75 | 158 ± 21 | 87 ± 8* | (3) 80 ± 3* | 258 ± 17 | 126 ± 13* | (3) 53 ± 6* |
| 20 | 180 ± 17 | 99 ± 6* | (13) 181 ± 19 | 208 ± 10 | 138 ± 15* | (13) 191 ± 9 |
| | | | (11) 120 ± 11* | | | (11) 190 ± 11 |
| | | | (14) 130 ± 15* | | | (14) 170 ± 22 |
| | | | (15) 100 ± 7* | | | (15) 153 ± 12* |
| 20 | 190 ± 23 | 105 ± 10* | (8) 152 ± 13 | 221 ± 12 | 172 ± 20 | (8) 214 ± 12 |
| | | | (9) 137 ± 15 | | | (9) 209 ± 15 |
| | | | (1) 160 ± 75 | | | (1) 186 ± 20 |
| | | | (2) 128 ± 15* | | | (2) 144 ± 20* |
| | | | (10) 79 ± 4* | | | (10) 106 ± 13* |
| | | | (11) 110 ± 7* | | | (11) 176 ± 15 |
| | | | (4) 130 ± 12* | | | (4) 192 ± 19 |
| | | | (16) 112 ± 11* | | | (16) 156 ± 20 |
| | | | (13) 149 ± 18 | | | (13) 227 ± 8 |

*significantly different from control values by unpaired test, p < 0.05.
**p < 0.05 when compared to the Standard and Example 2 product at the same dose.

Further testing of the non-salt product of Example 1 in ob/ob mice, following the same procedure with different dosing regimens demonstrated after administration of a single 75 mg./kg. oral dose followed by blood sampling in three hours post dosing, no significant difference between ciglitazone and vehicle control for either glucose or insulin; after dosing two days orally with 75 mg./kg. followed by blood sampling on the third day, both ciglitazone and the non-salt product of Example 1 demonstrated comparable, significant glucose and insulin reduction; and after daily oral dosing with 75 mg./kg. for nine days followed by blood sampling on the tenth day, the non-salt product of Example 1 demonstrated a more effective control of glucose and insulin levels than did the standard ciglitazone, as follows:

| 75 mg./kg. | Vehicle Control | Standard | Example 1 |
|---|---|---|---|
| Glucose (mg./dl.) | 120 ± 13 | 90 ± 8* | 68 ± 5* |
| Insulin (μU/ml.) | 152 ± 10 | 94 ± 13* | 75 ± 10* |

*p < 0.05 compared to control

In addition to the results given above, the products of Examples 2 and 3 and ciglitazone were studied in the db/db strain of diabetic mice. At doses of 75 mg./kg. orally once each day for four days, serum glucose levels in these severely hyperglycemic animals were decreased more than 50% with the product of Example 2 and more than 60% with the product of Example 3 while ciglitazone was ineffective.

The compounds of this invention also have anorectic properties related to the length of the perfluoro group, ranging from mild to marked, which provide further benefit to individuals diagnosed as Type II diabetics, or other obese members of the population on a subjective basis.

From the experimental data obtained, it is apparent that the compounds of this invention are potent anti-hyperglycemic and anti-hyperinsulinemic agents useful in the treatment of disease states characterized by abnormally high blood levels of glucose and/or insulin, such as diabetes mellitus and cardiovascular diseases, such as atherosclerosis. As such, the compounds of this invention are to be administered to a mammal suffering from excessive blood levels of glucose and/or insulin in an amount from about 5 mg./kg. to about 300 mg./kg. body weight or more per day. An optimum dosing regimen to achieve the desired therapeutic response must be individualized for the patient by following the post-administration glucose and/or insulin blood levels. The dosage will vary with the compound administered and with the patient's age, weight, severity of disease state, response, etc., as is common in all therapeutic methods for control of glucose and insulin levels. One advantage evidenced by the experimental testing of the compounds of this invention is that they tend only to normalize blood glucose levels, thereby avoiding any problem of precipitating hypoglycemic shock. In addition, the compounds of Examples 1 and 3 are more effective than the standard ciglitazone in reducing blood glucose levels.

The compounds of this invention are orally active and may be made up in conventional unit dosage forms for administration. Compositions with inert diluents or edible carriers are compressed into tablets or filled in hard or soft gelatin capsules, with sufficient active ingredients to supply a daily dose or any fraction thereof. Slow release formulations are especially suitable for control of glucose and insulin with the compounds of this invention.

What is claimed is:

1. A compound of the formula:

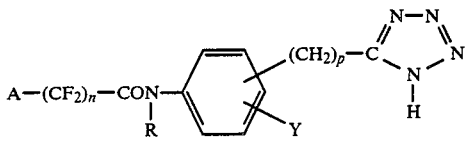

in which
R is hydrogen or A—$(CF_2)_m$—$CH_2$—;
A is —F or —H;
n is an integer from 1 to 10, inclusive;
m is an integer from 0 to 9, inclusive;
P is an integer from 0 to 4, inclusive; and
Y is hydrogen, halo, trifluoromethyl, alkyl of 1 to 6 carbon atoms, alkoxy of 1 to 6 carbon atoms or hydroxy;
or a pharmaceutically acceptable salt thereof.

2. The compound of claim 1 which is 2,2,3,3,4,4,4-heptafluoro-N-[4-(1H-tetrazol-5-ylmethyl)phenyl]butanamide, or a pharmaceutically acceptable salt thereof.

3. The compound of claim 1 which is 2,2,3,3,4,4,5,5,6,6,7,7,8,8,8-pentadecafluoro-N-[4-(1H-tetrazol-5-ylmethyl)phenyl]octanamide, or a pharmaceutically acceptable salt thereof.

4. The compound of claim 1 which is 2,2,3,3,4,4,5,5,6,6,7,7,8,9,9-hexadecafluoro-N-[4-(1H-tetrazol-5-ylmethyl)phenyl]nonanamide, or a pharmaceutically acceptable salt therof.

5. The compound of claim 1 which is 2,2,3,3,4,4,4-heptafluoro-N-[2-(1H-tetrazol-5-ylmethyl)phenyl]butanamide, or a pharmaceutically acceptable salt thereof.

6. The compound of claim 1 which is 2,2,3,3,4,4,4-heptafluoro-N-[3-(1H-tetrazol-5-ylmethyl)phenyl]butanamide, or a pharmaceutically acceptable salt thereof.

7. The compound of claim 1 which is 2,2,3,3,4,4,5,5,6,6,7,7,8,8,8-pentadecafluoro-N-[3-(1H-tetrazol-5-ylmethyl)phenyl]octanamide, or a pharmaceutically acceptable salt thereof.

8. The compound of claim 1 which is 2,2,3,3,4,4,4-heptafluoro-N-[4-(1H-tetrazol-5-yl)phenyl]butanamide, or a pharmaceutically acceptable salt thereof.

9. The compound of claim 1 which is 2,2,2-trifluoro-N-[4-(1H-tetrazol-5-ylmethyl)phenyl]acetamide, or a pharmaceutically acceptable salt thereof.

10. The compound of claim 1 which is 2,2,3,3,3-pentafluoro-N-[4-(1H-tetrazol-5-ylmethyl)phenyl]propanamide, or a pharmaceutically acceptable salt thereof.

11. The compound of claim 1 which is 2,2,3,3,4,4,5,5,6,6,7,7,8,8,9,9,9-heptadecafluoro-N-[4-(1H-tetrazol-5-ylmethyl)phenyl]nonanamide, or a pharmaceutically acceptable salt thereof.

12. The compound of claim 1 which is 2,2,3,3,4,4,5,5,6,6,7,7,8,8,9,9,10,10,10-nonadecafluoro-N-[4-(1H-tetrazol-5-ylmethyl)phenyl]decanamide, or a pharmaceutically acceptable salt thereof.

13. The compound of claim 1 which is 2,2,3,3,4,4,5,5,6,6,7,7,8,8,9,9,10,10,11,11-eicosafluoro-N-[4-(1H-tetrazol-5-ylmethyl)phenyl]undecanamide, or a pharmaceutically acceptable salt thereof.

14. The compound of claim 1 which is 2,2,3,3,4,4,5,5,5-nonafluoro-N-[4-(1H-tetrazol-5-ylmethyl)phenyl]pentanamide, or a pharmaceutically acceptable salt thereof.

15. The compound of claim 1 which is 2,2,3,3,4,4,4-heptafluoro-N-[4-(1H-tetrazol-5-ylethyl)phenyl]butanamide, or a pharmaceutically acceptable salt thereof.

16. The compound of claim 1 which is 2,2,3,3,4,4,5,5,6,6,7,7,8,8,8-pentadecafluoro-N-[4-(1H-tetrazol-5-ylpropyl)phenyl]octanamide, or a pharmaceutically acceptable salt thereof.

17. The compound of claim 1 which is 2,2,3,3,4,4,4-heptafluoro-N-[4-(1H-tetrazol-5-ylpropyl)phenyl]butanamide, or a pharmaceutically acceptable salt thereof.

* * * * *